(12) United States Patent
O'Carroll et al.

(10) Patent No.: US 11,654,025 B2
(45) Date of Patent: May 23, 2023

(54) DELIVERY DEVICE FOR AN ANNULOPLASTY IMPLANT

(71) Applicant: Medtentia International Ltd Oy, Espoo (FI)

(72) Inventors: Ger O'Carroll, Castlebaldwin (IE); Mark Pugh, Coolaney (IE); Stuart Deane, Rathrippin Collooney (IE); Chen Xie, Newbridge (IE); Jake O'Regan, Rathrippin Collooney (IE)

( * ) Notice: Subject to any disclaimer, the term of this patent is extended or adjusted under 35 U.S.C. 154(b) by 265 days.

(21) Appl. No.: 16/624,079

(22) PCT Filed: Jun. 18, 2018

(86) PCT No.: PCT/EP2018/066157
§ 371 (c)(1),
(2) Date: Dec. 18, 2019

(87) PCT Pub. No.: WO2018/234256
PCT Pub. Date: Dec. 27, 2018

(65) Prior Publication Data
US 2020/0205979 A1    Jul. 2, 2020

Related U.S. Application Data

(60) Provisional application No. 62/521,777, filed on Jun. 19, 2017.

(30) Foreign Application Priority Data

Jun. 19, 2017   (EP) .................................. 17176749

(51) Int. Cl.
*A61F 2/24*    (2006.01)
(52) U.S. Cl.
CPC .......... *A61F 2/2466* (2013.01); *A61F 2/2445* (2013.01); *A61F 2230/0091* (2013.01)

(58) Field of Classification Search
CPC .... A61F 2/2466; A61F 2/2445; A61F 2/2448; A61F 2/2442; A61F 2/2454; A61F 2/2457; A61F 2230/0091
See application file for complete search history.

(56) References Cited

U.S. PATENT DOCUMENTS 6,936,058 B2    8/2005    Forde
7,959,661 B2    6/2011    Hijlkema
(Continued)

FOREIGN PATENT DOCUMENTS

EP    2072027 A1    6/2009
EP    1408850 B1    9/2009
(Continued)

OTHER PUBLICATIONS

International Search Report for International Application No. PCT/EP2018/066157, dated Aug. 17, 2018 (2 pages).

*Primary Examiner* — Keri J Nelson
*Assistant Examiner* — Rebecca Lynee Zimmerman
(74) *Attorney, Agent, or Firm* — Patent Grove AB; Tomas Friend (57) ABSTRACT

A delivery device for an annuloplasty implant is disclosed comprising an outer sheath, a delivery wire being movable within said sheath in a longitudinal direction thereof, a holder being releasably connectable to said implant, said holder being pivotably connected to a distal portion of said delivery wire, wherein said holder is folded inside said outer sheath in a delivery configuration, and wherein said holder is foldable from said delivery configuration to an expanded deployed configuration outside said outer sheath. A system comprising such delivery device and an annuloplasty implant, and a method of delivering such implant is also disclosed.

26 Claims, 10 Drawing Sheets

(56) References Cited

U.S. PATENT DOCUMENTS

| | | |
|---|---|---|
| 8,652,202 B2 | 2/2014 | Alon |
| 9,155,619 B2 | 10/2015 | Liu |
| 2003/0050693 A1* | 3/2003 | Quijano ................ A61F 2/2445 623/2.11 |
| 2005/0033446 A1 | 2/2005 | Deem |
| 2015/0374493 A1 | 12/2015 | Yaron et al. |
| 2016/0030176 A1 | 2/2016 | Mohl et al. |
| 2016/0045312 A1* | 2/2016 | Braido .................. A61B 5/026 623/2.37 |
| 2017/0156859 A1 | 6/2017 | Chang |
| 2020/0100898 A1* | 4/2020 | Vola ..................... A61F 2/2445 |

FOREIGN PATENT DOCUMENTS

| | | |
|---|---|---|
| EP | 2412316 A2 | 2/2012 |
| EP | 3120811 A2 | 1/2017 |
| WO | 2003047467 A1 | 6/2003 |
| WO | 2006116558 A2 | 11/2006 |
| WO | 2013059776 A1 | 4/2013 |
| WO | 2013114214 A2 | 8/2013 |
| WO | 2014190329 A1 | 11/2014 |
| WO | 2015023862 A2 | 2/2015 |
| WO | 2018195215 A2 | 10/2018 |

* cited by examiner

DELIVERY DEVICE FOR AN ANNULOPLASTY IMPLANT

CROSS-REFERENCE TO RELATED APPLICATIONS

This application claims priority to International Application No. PCT/EP2018/066157, filed Jun. 18, 2018 and titled "DELIVERY DEVICE FOR AN ANNULOPLASTY IMPLANT," which in turn claims priority from a European Patent Application having application number 17176749.4, filed Jun. 19, 2017, titled "DELIVERY DEVICE FOR AN ANNULOPLASTY IMPLANT," and U.S. Provisional Application No. 62/521,777, filed Jun. 19, 2017, titled "DELIVERY DEVICE FOR AN ANNULOPLASTY IMPLANT," all of which are incorporated herein by reference in their entireties.

TECHNICAL FIELD

This invention pertains in general to the field of cardiac valve replacement and repair. More particularly the invention relates to a medical device for delivering a catheter deliverable cardiac valve implant, a system comprising such delivery device and implant, such as an annuloplasty ring, and a method of delivering such implant.

BACKGROUND

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. Such annuloplasty rings or other annuloplasty implants are put into position by various delivery devices.

A problem with prior art delivery devices is lack of steerability or maneuverability of the implant, thereby increasing the amount of manipulation of the implant both during the positioning phase and during repositioning to get the implant in the correct position, which may lead to a more complicated and time consuming procedure. During heart surgery, a premium is placed on reducing the amount of time used to replace and repair valves as the heart is frequently arrested and without perfusion.

A further problem with prior art devices is less-than-optimal engagement mechanisms between the implant and the delivery wire that does not provide sufficient reliability, and/or requires exact, i.e. time consuming, navigation and manipulation before final securement is achieved.

The above problems may have dire consequences for the patient and the health care system. Patient risk is increased.

Hence, an improved medical device for delivering an annuloplasty implant would be advantageous and in particular allowing for avoiding more of the above mentioned problems and compromises, and in particular allowing for increased maneuverability, reducing the time of lengthy surgery procedures, cost effectiveness, and increased patient safety. Also, a system comprising such device and an annuloplasty implant, and a method of delivering such implant would be advantageous.

SUMMARY OF THE INVENTION

Accordingly, examples of the present invention preferably seeks to mitigate, alleviate or eliminate one or more deficiencies, disadvantages or issues in the art, such as the above-identified, singly or in any combination by providing a device according to the appended patent claims.

According to a first aspect a delivery device for an annuloplasty implant is provided. The delivery device comprises an outer sheath, and a delivery wire being movable within said sheath in a longitudinal direction thereof, a holder being releasably connectable to said implant, said holder being pivotably connected to a distal portion of said delivery wire, wherein said holder is folded inside said outer sheath in a delivery configuration, and wherein said holder is foldable from said delivery configuration to an expanded deployed configuration outside said outer sheath.

According to a second aspect a system comprising a delivery device according to the first aspect and an annuloplasty implant is provided, wherein said annuloplasty implant is formed from a shape memory material and having a relaxed general ring shape when implanted, and a stretched elongated shape for delivery in said sheath, wherein said implant is pivotable outside said sheath by moving said holder from said delivery configuration to said expanded deployed configuration.

According to a third aspect a method for delivering an annuloplasty implant with a delivery device is provided. The delivery device has a holder being pivotably connected to a distal portion of a delivery wire inside a sheath, and the holder being releasably connectable to said implant. The method comprises holding said implant inside said sheath whereby said holder is folded inside said sheath in a delivery configuration; moving said holder distally out of said sheath whereby said implant being formed from a shape memory material assumes a pre-defined shape; folding said holder from a said delivery configuration to an expanded deployed configuration outside said sheath whereby said implant is pivoted by said holder into position at a heart valve.

Further examples of the invention are defined in the dependent claims, wherein features for the second and subsequent aspects of the disclosure are as for the first aspect mutatis mutandis.

Some examples of the disclosure provide for facilitated delivery of an annuloplasty implant to a target site.

Some examples of the disclosure provide for increased steerability or maneuverability of an annuloplasty implant.

Some examples of the disclosure provide for less time consuming positioning of an annuloplasty implant at a target site in the heart.

Some examples of the disclosure provide for less cumbersome attachment and detachment of an annuloplasty implant to a medical delivery device.

Some examples of the disclosure provide for increased accuracy in positioning an annuloplasty implant at the annulus and thereby reducing the risk of complications.

Some examples of the disclosure provide for a reduced risk of damaging the cardiac valve implant during a repair or replacement procedure.

Some examples of the disclosure provide for better ability to reposition an annuloplasty implant.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of embodiments of the present invention, reference being made to the accompanying drawings, in which.

DETAILED DESCRIPTION

Specific examples of the invention will now be described with reference to the accompanying drawings. This invention may, however, be embodied in many different forms and should not be construed as limited to the examples set forth herein; rather, these examples are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on examples applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 1A:
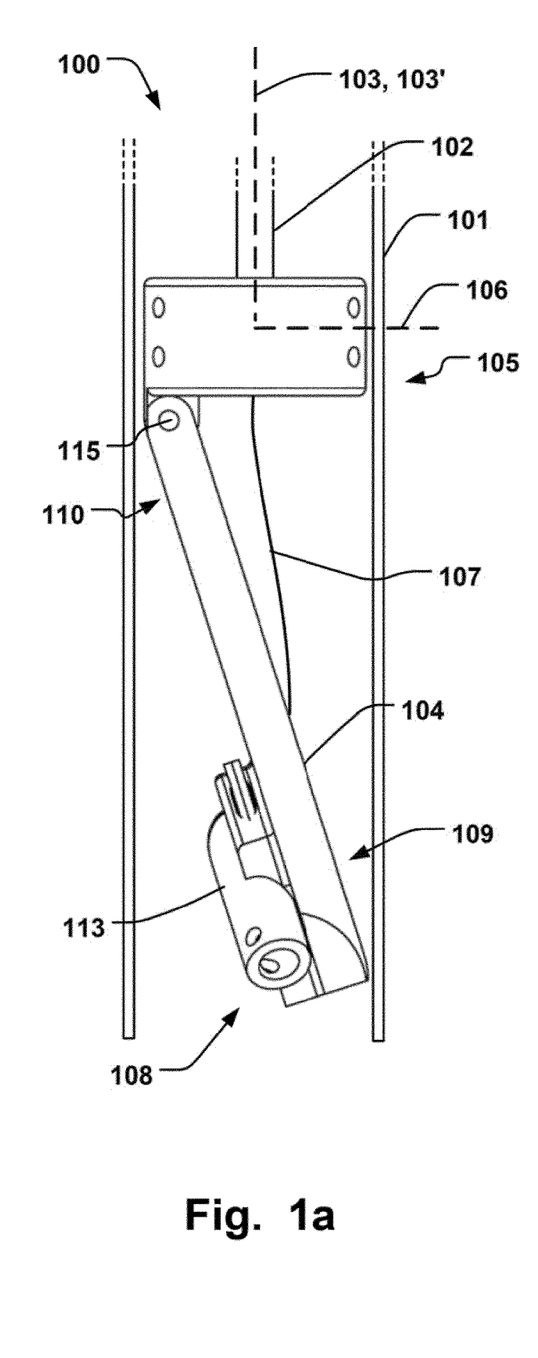
FIG. 1a is a schematic illustration, in a side view, of a delivery device according to one example.
Figures 3A, 3B, 3C:
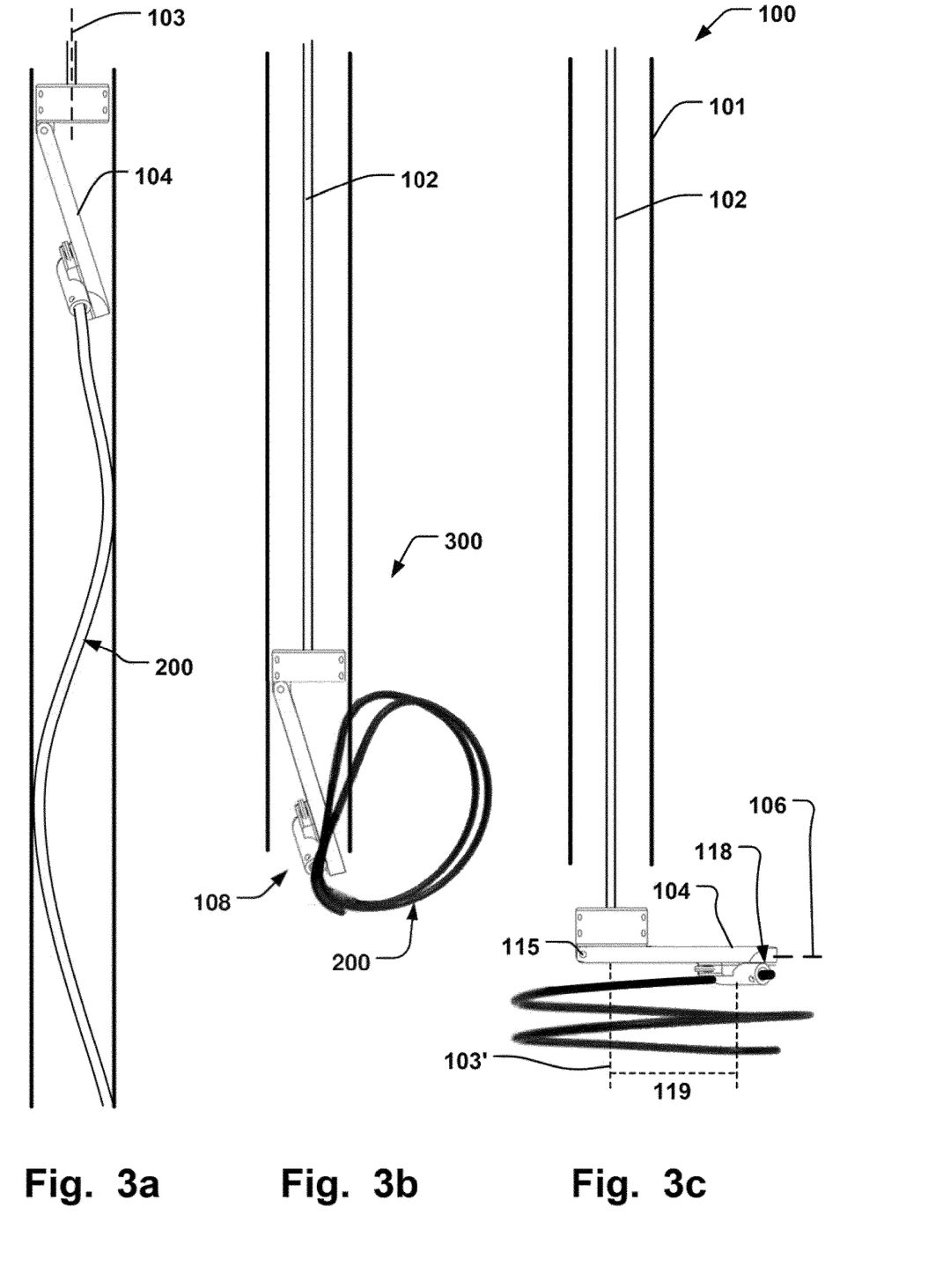
FIGS. 3a-c are schematic illustrations, in side views, of a delivery device holding an annuloplasty implant according to one example.

FIG. 1a illustrates an example of a delivery device 100 for an annuloplasty implant 200 (not shown). The delivery device 100 comprises an outer sheath 101, and a delivery wire 102 being movable within the sheath 101 in a longitudinal direction 103 of the outer sheath 101. The delivery device 100 comprises a holder 104 being releasably connectable to the implant 200. The holder 104 is pivotably connected, i.e. having a rotating connection, to a distal portion 105 of the delivery wire 102. Thereby, the holder 104 is able to be folded inside the outer sheath 102 in a delivery configuration, which is illustrated in FIGS. 1a-b, and FIGS. 3a-b. The holder 104 is in the delivery configuration when the delivery device 100 is being navigated to the target site at which the implant 200 is to be positioned. The holder 104 is foldable from the delivery configuration to an expanded deployed configuration outside the outer sheath 101, which is illustrated in FIG. 3c. By having a holder 104 being pivotably connected at a distal portion 105 of the delivery wire 102, and thereby foldable between a delivery configuration and an expanded deployed configuration, it is possible to attain a compact shape during the delivery procedure, whereas a robust and highly torquable configuration is achieved in the expanded state, when the implant 200 is to be deployed. It is thus easy to transfer force at the operator end to the distal portion of the delivery device 100 where the implant 200 is attached, allowing for a high steerability and maneuverability at the target site. This can reduce the time of the implantation procedure and therefore generally allow for a more safe intervention. The pivoting connection allows for facilitated transfer from the collapsed delivery configuration inside the outer sheath 101 to the expanded deployed configuration, requiring a minimum amount of force.

FIGS. 3a-c schematically illustrate the implant 200 being delivered from the delivery device 100. In FIG. 3a the holder 104 is folded inside the outer sheath 101, and releasably holds the implant 200 at a distal end thereof. The implant 200 is in this case formed from a shape memory material and is flexible enough to be stretched in the longitudinal direction 103 of the outer sheath 101. In FIG. 3b, the delivery wire 102 has pushed the holder 104 further towards the distal end of the delivery device 100. The holder 104 is in this case about to be pushed out and removed from the radial constraint of the outer sheath 101, and the implant 200 has already been expelled from the sheath 101, and is thereby allowed to assume the pre-defined relaxed shape of the shape memory material from which it is formed. In this case, the implant 200 is an annuloplasty ring, intended to be positioned around the annulus of a heart valve. FIG. 3c illustrates the case where the delivery wire 102 has pushed the holder 104 to a position outside the sheath 101, and the holder 104 has been folded from the delivery configuration to the expanded deployed configuration by a rotating motion of the holder 104 relative the delivery wire 102. Since the implant 200 is releasably held by the holder 104, the implant 200 is also rotated relative the delivery wire 102. The degree of rotation of the implant 200 thereby substantially corresponds to the degree of rotation of the holder 104, as the implant 200 is substantially rigidly fixated at the holder 104. As mentioned above, this allows for a high degree of maneuverability of the implant 200. For example, torque may be effectively transferred to the implant 200, since the holder 104 is now in the expanded configuration. Rotation of the implant 200 for example around the longitudinal axis 103 of the sheath 102 can thereby be facilitated. The implant 200 may also be controllably rotated a desired amount around the axis of the pivoting connection of the holder 104, which is exemplified by pivoting connection 115 in FIG. 3c. Thus, rotation of the implant 200 around such multiple axes provides for an optimized steerability and facilitating positioning of the implant 200 at the target site. In particular, for annuloplasty implants, the space around the valve annulus in the heart is a tightly confined space requiring such increased maneuverability provided by the delivery device 100, in order to position the implant 200 at the correct angle relative the plane of the valve and the associated annulus. Turning to FIG. 3c again, illustrating an example of holding an annuloplasty ring 200, such ring 200 can now be manipulated to be positioned in the correct plane, e.g. by rotation around the pivotable connection to the delivery wire, and subsequently rotated around the longitudinal axis 103 of the sheath 101 in order to be rotated in place around the tissue of the annulus. The latter is particularly advantageous for helix- or coiled shaped annuloplasty rings, as illustrated in FIG. 3c, since these rings can then be rotated through the commissures as the valve so that the lower ring is positioned beneath the valve leaflets, and the top ring is positioned above the valve leaflets. Such helix shaped implants 200 can thus be effectively delivered in the correct position at the annulus by the delivery device 100 as well as being delivered to the target site through the narrow space available due to the compact delivery shape of the holder 104, and the compact mechanism for transferring the holder 104 to the expanded deployed configuration outside the sheath 101, by the pivotable connection.

Figure 4A:
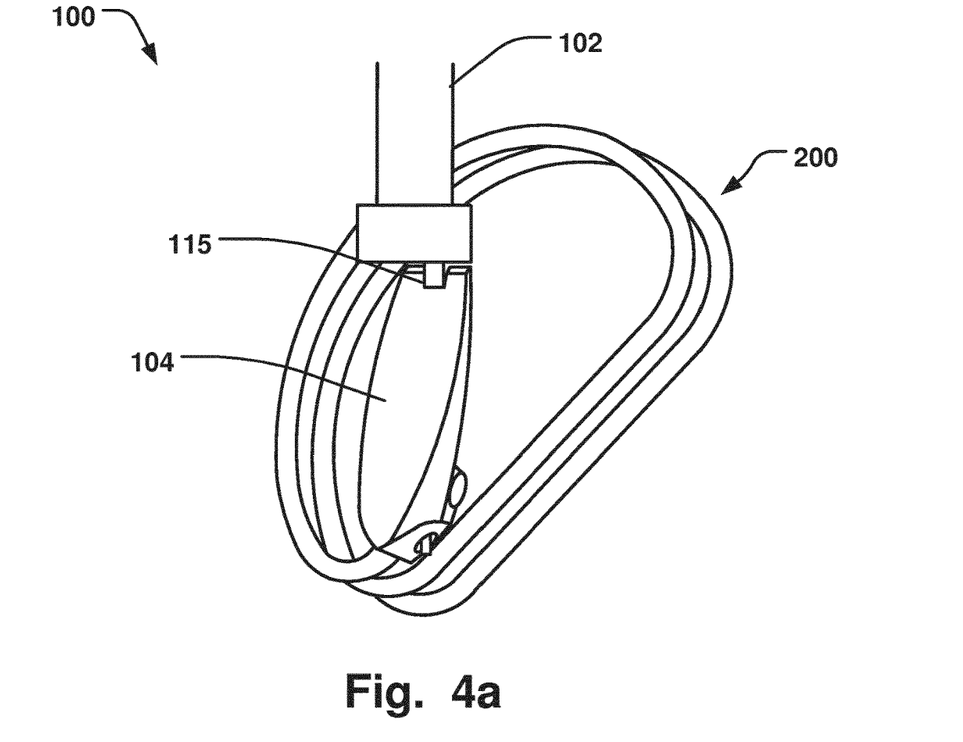
FIGS. 4a-d are schematic illustrations, in perspective views, of a delivery device holding an annuloplasty implant according to one example.
Figure 4B:
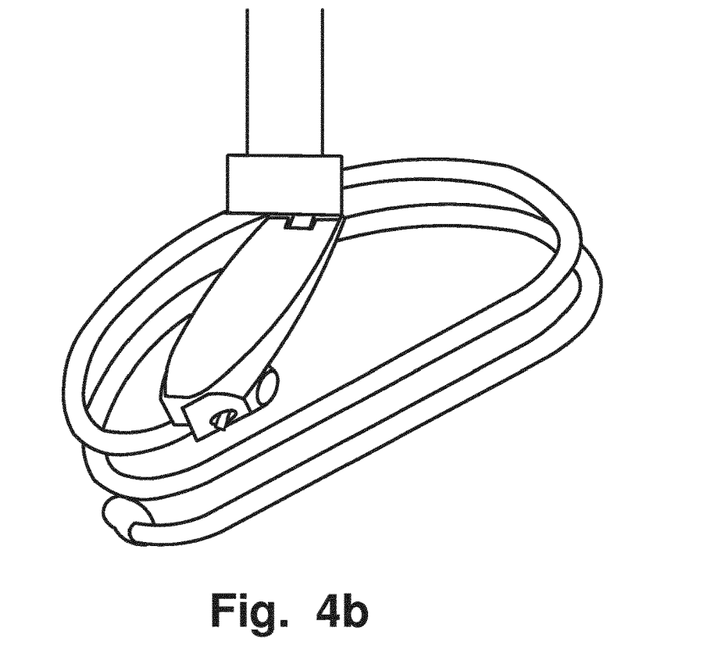
Figure 4C:
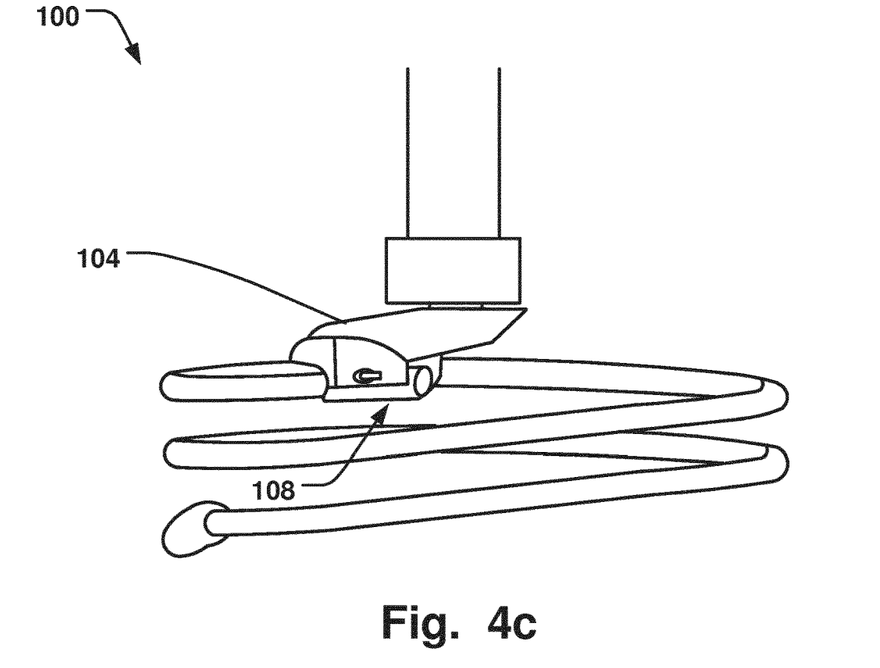
Figure 4D:
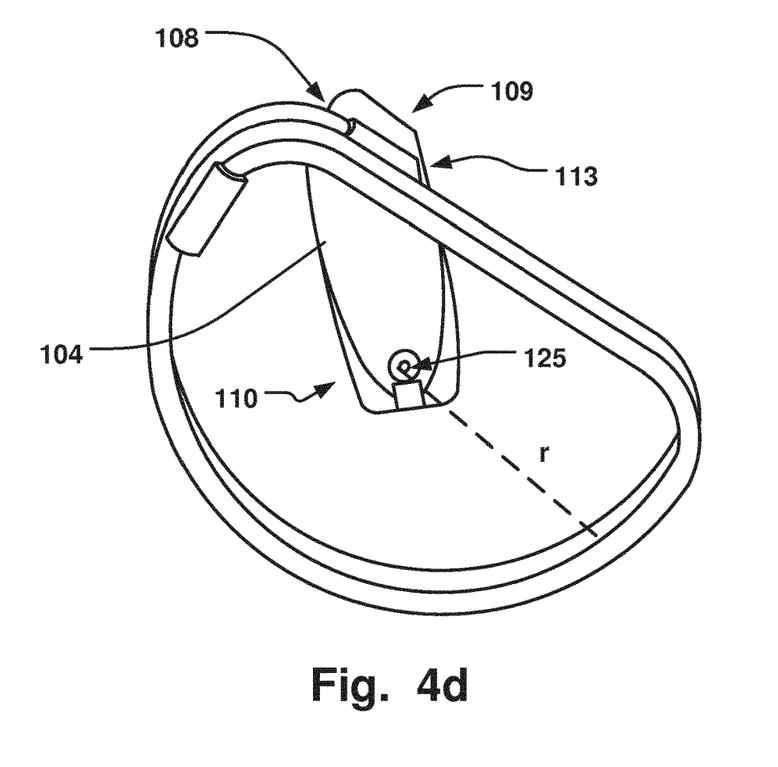

FIGS. 4a-c, show examples where the holder 104 is rotated in varying angles relative the delivery wire 102. In these examples, the outer sheath 101 has been removed for clarity of presentation. The implant 200, being an annuloplasty ring 200, is shown in the expanded pre-defined relaxed configuration. FIGS. 4a and 4c show the least and most amount of rotation, respectively, with FIG. 4b in between. FIG. 4d is a view from beneath the distal end of the delivery device 100 when in the maximum expanded configuration.

Figure 5A:
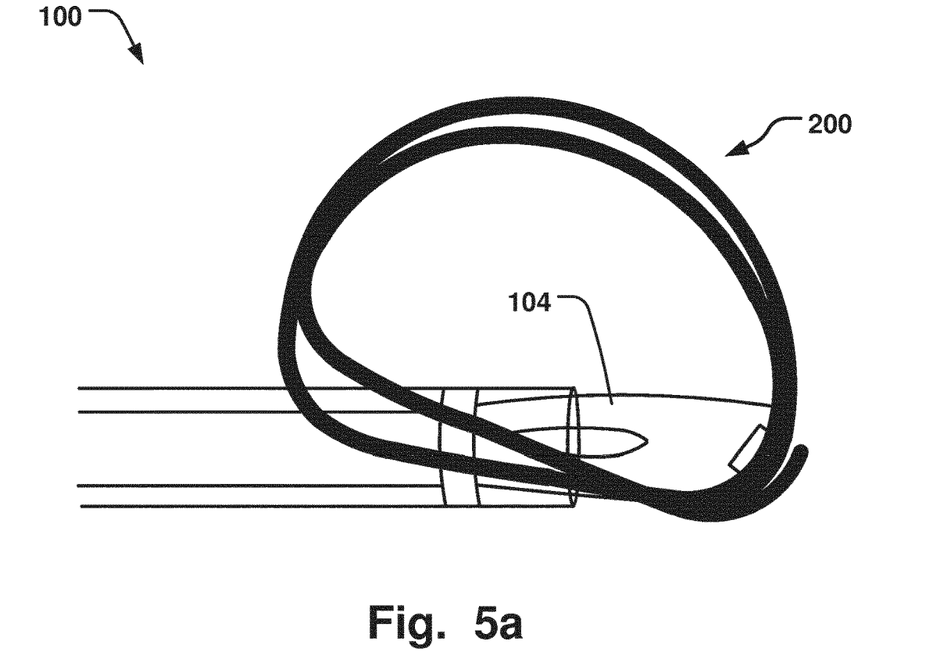
FIGS. 5a-b are schematic illustrations, in perspective views, of a delivery device holding an annuloplasty implant according to one example.
Figure 5B:
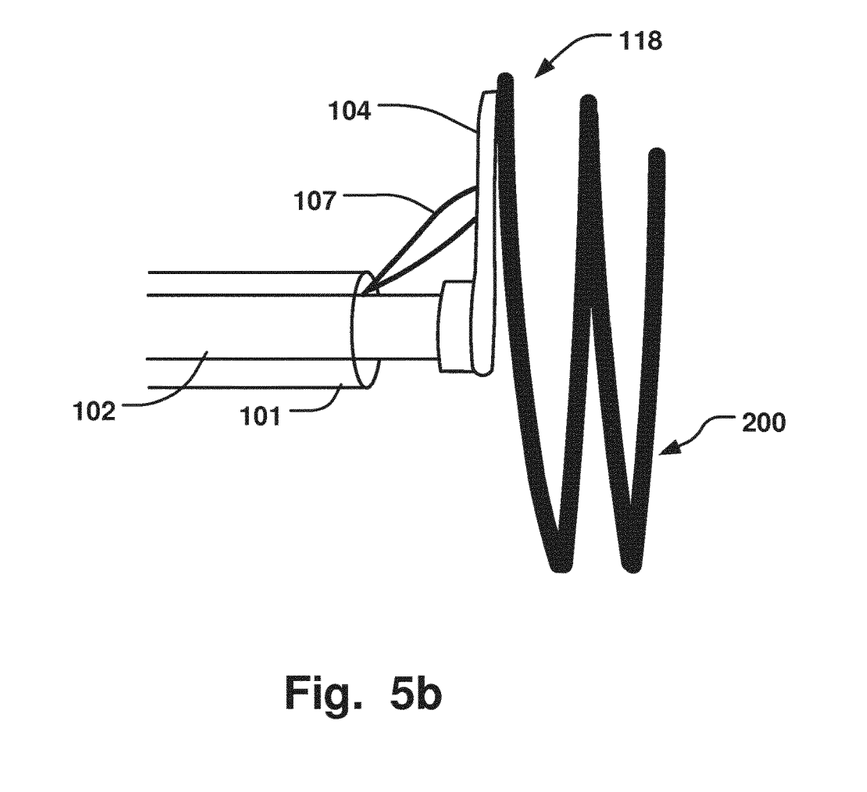

FIGS. 5a-b show the delivery device 100 in similar configurations to those of FIGS. 3b-c, respectively, but in further enlarged views.

Figure 6A:
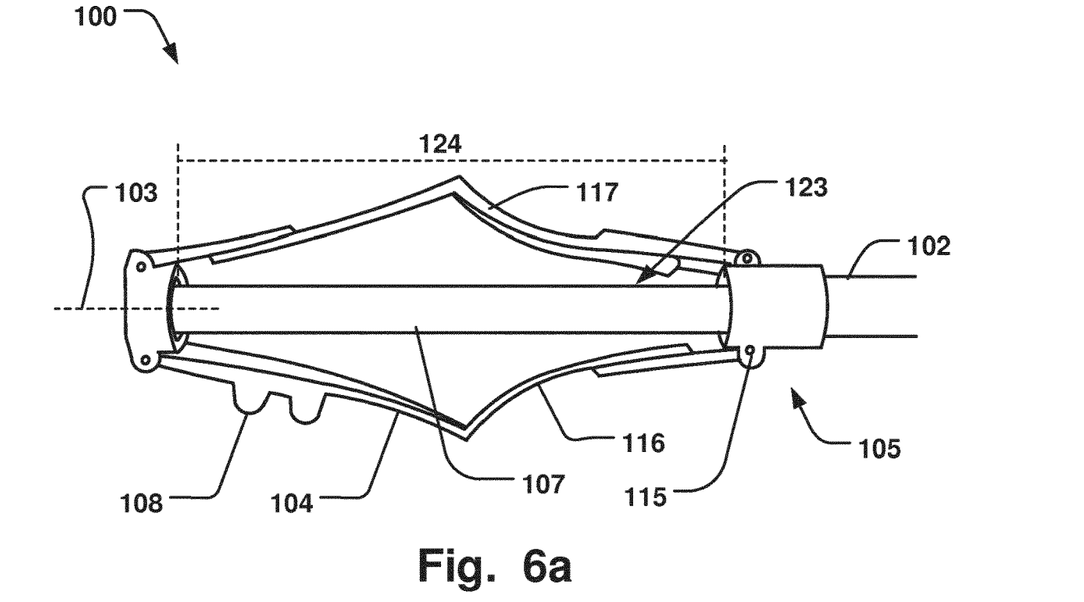
FIGS. 6a-b are schematic illustrations, in perspective views, of a delivery device according to one example.
Figure 6B:
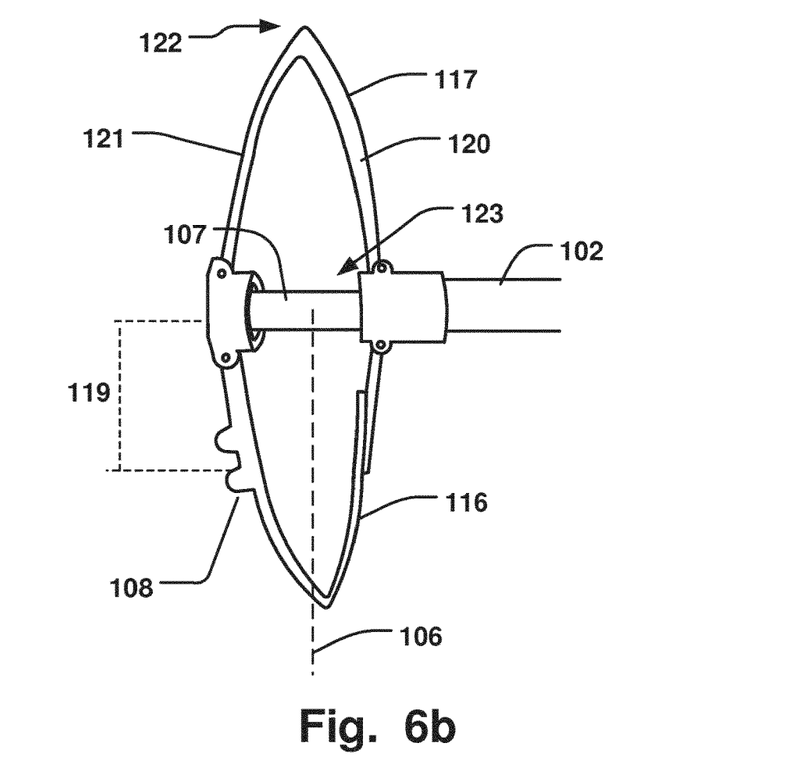
Figure 8A:
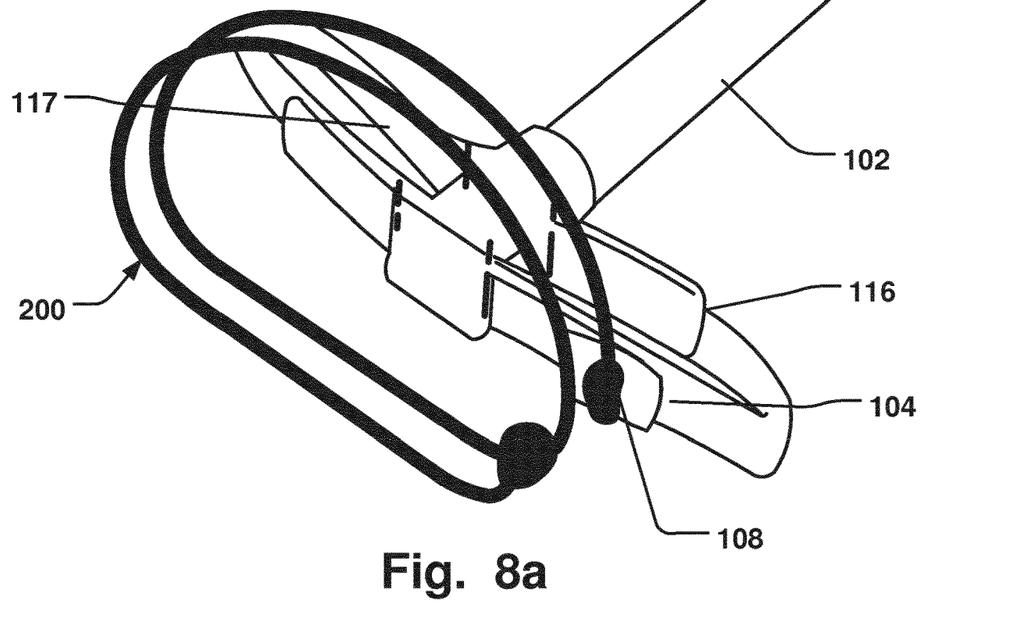
FIG. 8a is a schematic illustration, in a perspective view, of a delivery device in FIGS. 6a-b holding an annuloplasty implant.

FIGS. 6a-b show other examples of the delivery device 100. As described above, the device 100 has a delivery wire 102, and a holder 104 which can releasably connect to an implant 200, which is shown in FIG. 8a. The holder 104 is pivotably connected to a distal portion 105 of the delivery wire 102, at pivoting connection 115. The holder 104 can be moved from a folded configuration, like the configuration illustrated in FIG. 6a, to an expanded deployed configuration, like the configuration illustrated in FIG. 6b, by rotating around the pivoting connection 115. As with the delivery device 100 illustrated in FIGS. 1-5, the implant 200 will also be rotated when held by the holder 104 in the delivery device 100 of FIGS. 6a-b, with the similar advantages as already described above. The outer sheath 102 has been omitted in FIGS. 6a-b for clarity of presentation.

Figure 1B:
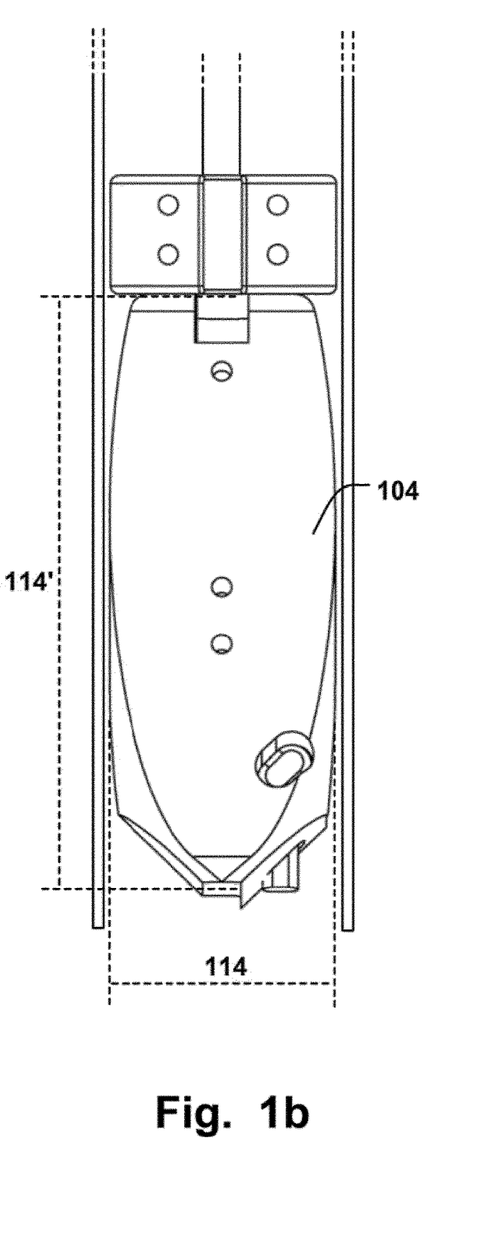
FIG. 1b is a schematic illustration, in a side view rotated 90 degrees relative FIG. 1a, of a delivery device according to one example.

The holder 100 may be elongated and extending in the longitudinal direction 103 of the sheath 101 in the delivery configuration, as seen for example in FIGS. 1a-b. By having an elongated holder 104, the holder 104 assumes a compact cross-sectional dimension perpendicular to the longitudinal direction 103, while providing significant reach and torque abilities when extending in a radial direction 106, perpendicular to the longitudinal direction 103, in the expanded deployed configuration. The implant 200 may be releasably connected at the distal end 109 of the holder 104, which facilitates the rotation of the implant 200 when the holder 104 is in the expanded deployed configuration.

The delivery device 100 may comprise a control member 107, such as a control wire 107, connected to the holder 104, as schematically illustrated in FIG. 1a. Actuation of the control member 107 moves the holder 104 from the delivery configuration to the expanded deployed configuration by a pivoting motion. Actuation of the control member 107 can be a pulling action of the control member 107 towards the proximal end of the delivery device 100, so that the control member 107 lifts the holder 104 to the expanded deployed configuration as seen in FIG. 3c. Similarly, the control member 107 may be pushed towards the distal end 109, in order to move the holder 104 from the expanded deployed configuration to the delivery configuration in which the holder is folded to extend in the longitudinal direction 103, to be withdrawn into the sheath 101, as illustrated in FIGS. 3a-b. It is also conceivable that the control member 107 can be actuated in other ways, such as for example by a rotating motion, that affects the movement of the holder 104 by a screw-like or winding motion, so that the holder 104 is lifted to the expanded deployed configuration, or in the opposite direction for folding inside the sheath 101. FIG. 5b also illustrates the control member 107, extending from the delivery wire 101 or the outer sheath 102, to the holder 104. The control member 107 may be attached to a position of the holder 104 that provides for a facilitated actuation thereof. Having the attachment point positioned closer to the radial periphery of the holder, when in the expanded configuration, can provide for reducing the force required to deploy the holder 104 in the expanded deployed configuration. The control member 107 may be actuated by a predetermined amount in order to precisely control the amount of rotation of the holder 104, and thereby the amount of rotation of the implant 200, to position the implant 200 in the correct position at the target site.

FIGS. 6a-b shows an example where the control member 107 is centrally connected to a distal portion of the holder 104, for either pushing the central distal portion of the holder 104, distally, towards a distal end of the delivery device 100, relative the delivery wire 102, so that the holder 104 assumes the elongated shape in the longitudinal direction 103 as exemplified in FIG. 6a, or pulled relative the delivery wire 102, so that the holder 104 is folded to the expanded configuration, as exemplified in FIG. 6b.

The holder 104 may comprise a connecting unit 108, which is illustrated in e.g. FIGS. 1a, 2, 6a, and 8a, that is adapted to releasably connect to the implant 200. Releasably connected should be construed as the implant 200 can be readily released from the connecting unit. The connecting unit 108 may be arranged at a distal end 109 of the holder, as seen in e.g. FIG. 2. This allows for utilizing the full length of the holder 104 for improving the maneuverability of the implant 200, i.e. facilitating the positioning of the implant 200, while attaining a compact profile of the delivery device, particularly in the expanded deployed configuration.

The delivery wire 102 may be rotatable relative the sheath 101, i.e. around a central axis 103' of the sheath 101. The connecting unit 108 may be adapted to apply a force at a peripheral portion 118 of the implant 200, at a distance 119 from the central axis 103' of the sheath 101 when the implant 200, in use, is held by the holder 104 in the expanded deployed configuration, such that the force can bring the implant into rotation about the central axis 103'. Thus, torque can be transferred from the rotation of the delivery wire 102, relative the sheath 101, to the implant 200 via the connecting unit 108. Rotation of the implant 200 into the correct position is thus facilitated. The connecting unit 108 can be adapted to connect to the implant 200, such as an annuloplasty ring, at the peripheral portion 118 of the ring.

The length 114' of the elongated holder 104, as illustrated in FIG. 1b, may correspond substantially to a radius (r) of the implant 200, when the implant 200, in use, is held by the holder in the expanded deployed configuration and the implant has a general ring shape with the radius (r), i.e. when being an annuloplasty ring. As illustrated in FIG. 4d, this may provide for an optimal length 114' of the holder 104, which will provide for a compact profile while allowing the distal end 109 of the holder to be fixated at the periphery 118 of the implant 200, improving the steerability. The distance 119 from the center of the sheath 101 to the connecting unit 108 may thus substantially correspond to the radius (r) of the annuloplasty ring 200.

The connecting unit 108 may be adapted to connect to an end portion 113 of the implant 200, as illustrated in FIG. 4d. The connecting unit 108 may be aligned at a distal end 109 of the holder 104 so that a proximal end 110 of the holder 104 is position substantially at the center 125 of the implant 200, when the implant 200, in use, is held by the holder 104 in the expanded deployed configuration and the implant has a general ring shape with the center 125, i.e. being an annuloplasty ring. A concentric rotation of the ring 200 around the central axis 103' of the sheath 101 can thereby be provided. This improves the control of the rotating motion of the implant 200, since it can be predictably moved by a rotating motion only, i.e. minimizing any translatory motion, when rotating the delivery wire 102 to position the implant 200 at the target site. In particular, when rotating the ring 200 through the commissures of the valve, it can be preferable to avoid movement of the ring in other directions at the valve. This can also minimize the risk of damaging the surrounding anatomy. The connecting unit 108 may thus be angled relative the holder 104, see further FIG. 2, to allow such positioning of the proximal end 110 at the center 125 of the ring 200, corresponding substantially to the location of the central axis 103'.

Figure 2:
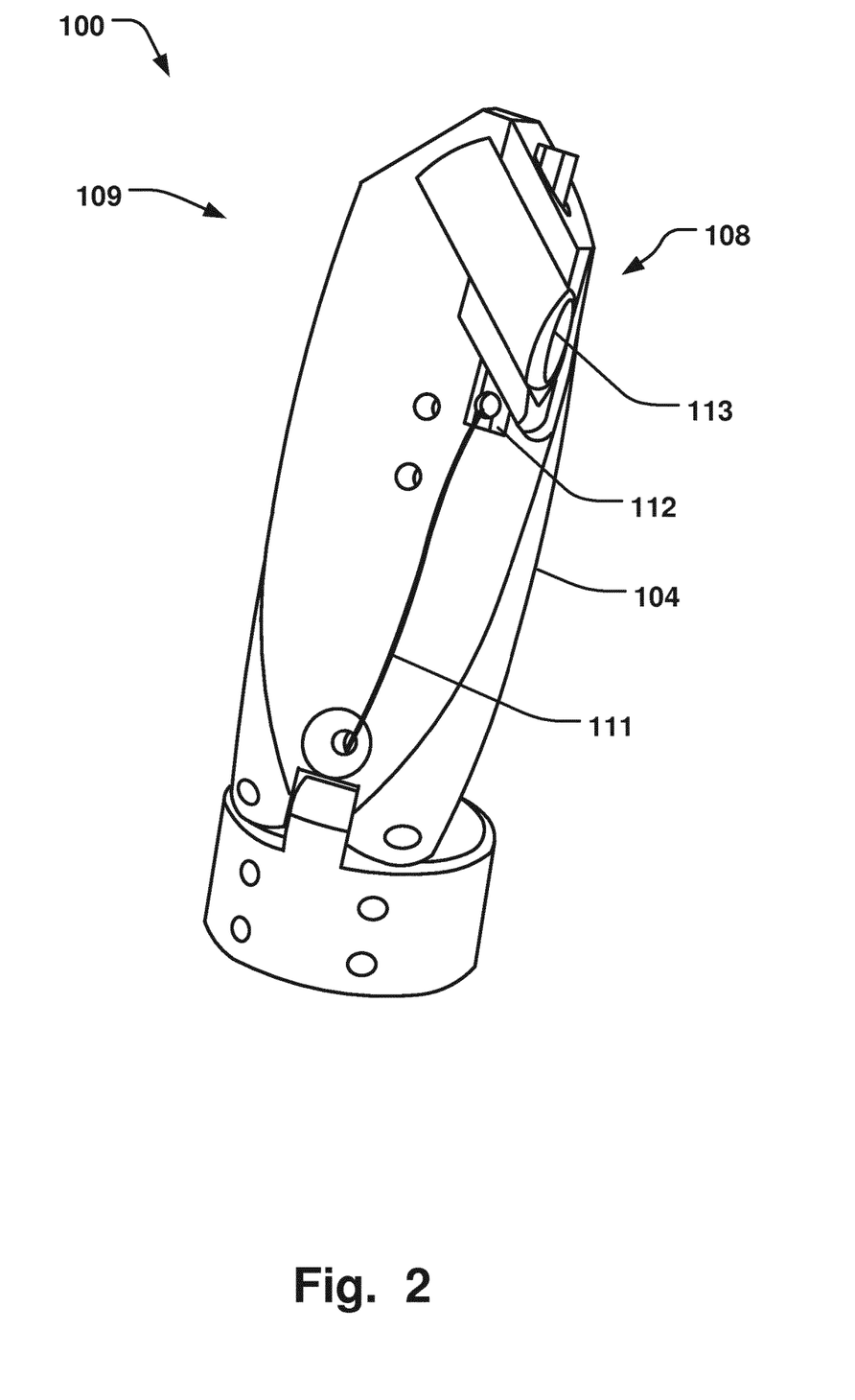
FIG. 2 is a schematic illustration, in a perspective view, of a delivery device according to one example.

The connecting unit 108 may be connected to a release unit 111, such as a release wire 111, illustrated in FIG. 2. Actuation of the release unit 111 may release the implant 200 from the holder 104 by disengaging an implant lock 112. This provides for a reliable and robust delivery of the implant 200. The implant look 112 may be adapted to interlock with an end portion 113 of the implant 200, also illustrated in FIG. 2. Here only the end portion 113 is illustrated for clarity of presentation, but the end portion 113 is fixated to the implant 200. The implant look 112 may for example engage with an aperture, recess, protrusion or a flat surface in the end portion 113, from which it can be removed to release the implant 200.

Thus, the implant lock 112 may be engageable with an end portion 113 of the implant 200, when the implant 200, in use, is held by the holder 104.

The width 114 of the holder 104, i.e. its dimension in the radial direction perpendicular to the longitudinal direction 103, may correspond substantially to the diameter of the outer sheath 101, as illustrated in FIG. 1b. This may provide improve stability of the holder 104 when operated.

The holder 104 may be pivotably connected at a pivot joint 115 arranged at the distal portion 105 of the delivery wire 102. The pivot joint 115 may be arranged at a periphery of the distal portion in a radial direction 106, perpendicular to the longitudinal direction 103, which is illustrated in FIG. 1a. It is thus possible to achieve a greater momentum when actuating the control member 107, for example by pulling the control member 107 towards the proximal end of the delivery device 100, i.e. towards the operator end, in order to lift the holder 104 to the expanded deployed configuration as seen in FIG. 3c. It will thus be easier to pivot the holder 104 into this configuration due to the increased distance between the central axis 103' of the sheath 101 and the pivot joint 115, since the latter is positioned adjacent the periphery of the distal portion 105 of the delivery wire 102. The increased distance from the pivot joint 115 to the central axis 103 contributes to an overall increase in distance between the pivot joint 115 and the fixation point of the control member 107 at the holder 104, which advantageously is positioned in the opposite radial direction, with respect to the pivot joint. I.e. the pivot joint 115 and the mentioned fixation point will be positioned at radially opposite sides with the central axis 103' of the sheath 101 inbetween.

Figure 8B:
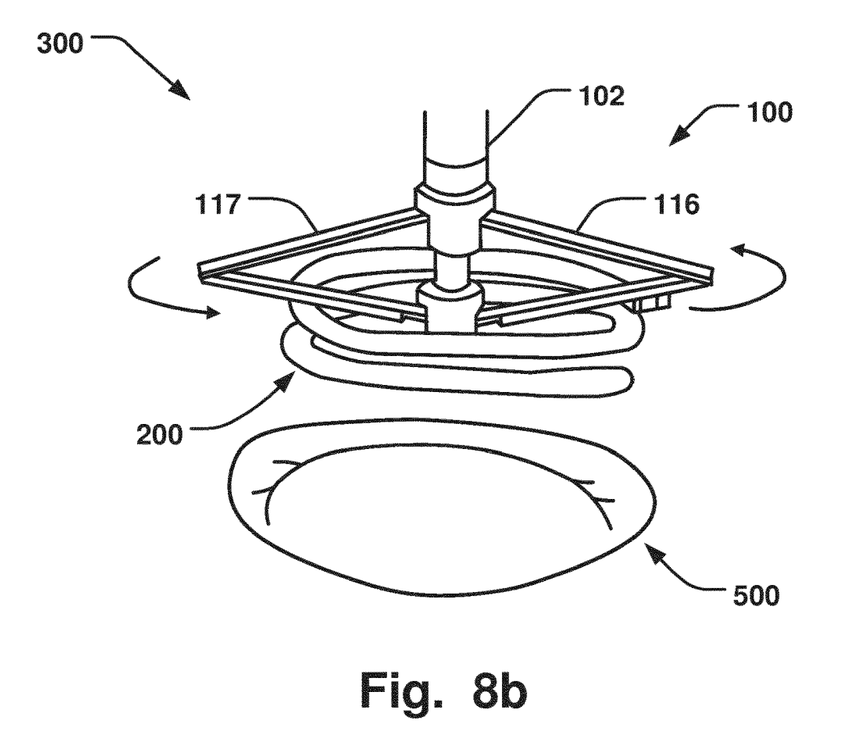
FIG. 8b is a schematic illustration, in a perspective view, of a delivery device in FIGS. 6a-b holding an annuloplasty implant at a heart valve according to one example.

Turning again to FIGS. 6a-b, the holder 104 may have a first 116 and a second 117 pivotable portion, each being expandable in radially opposite directions in the expanded deployed configuration along the radial direction 106, as illustrated in FIGS. 6b and 8a-b. This provides for a robust and stable delivery device 100, and both of the pivotable portions 116, 117, may act as supporting members for the implant 200, when in the expanded deployed configuration, as schematically illustrated in FIG. 8b. Undesired tilting of the implant 200 may thus be prevented when navigating the implant 200 to the correct position over the heart valve 500.

Each of the first and second pivotable portions 116, 117, may comprise foldable proximal 120 and distal 121 sections forming V-shaped first and second pivotable portions 116, 117, each having an apex 122 at a radially outward position, along the radial direction 106, and a base 123 at a radially inward position. This is illustrated in FIG. 6b, where each of the pivotable portions 116, 117, have such foldable proximal 120 and distal 121 sections forming a V-shaped portion. The length 124 of the base 123 is adjustable by moving the control member 107 relative the delivery wire 102, as illustrated in FIG. 6a, where the control member 197 has been pushed further towards the distal end of the delivery device 100, relative the delivery wire 102, so that the base 123 has a longer length 124 compared to the configuration in FIG. 6b. The proximal and distal sections 120, 121, are thus foldable between the delivery configuration and the expanded deployed configuration by adjusting the length 124 of the base 123. Thus further provides for a simple and reliable mechanism for transferring the delivery device between the two mentioned configurations.

A system 300 is provided comprising a delivery device 100 as described according to the examples above and an annuloplasty implant 200. The annuloplasty implant 200 may be formed from a shape memory material and having a relaxed general ring shape when implanted, and a stretched elongated shape for delivery in the sheath, wherein the implant is pivotable outside the sheath 101 by moving the holder 104 from the delivery configuration to the expanded deployed configuration, as explained above and with the above mentioned advantages.

Figure 7:
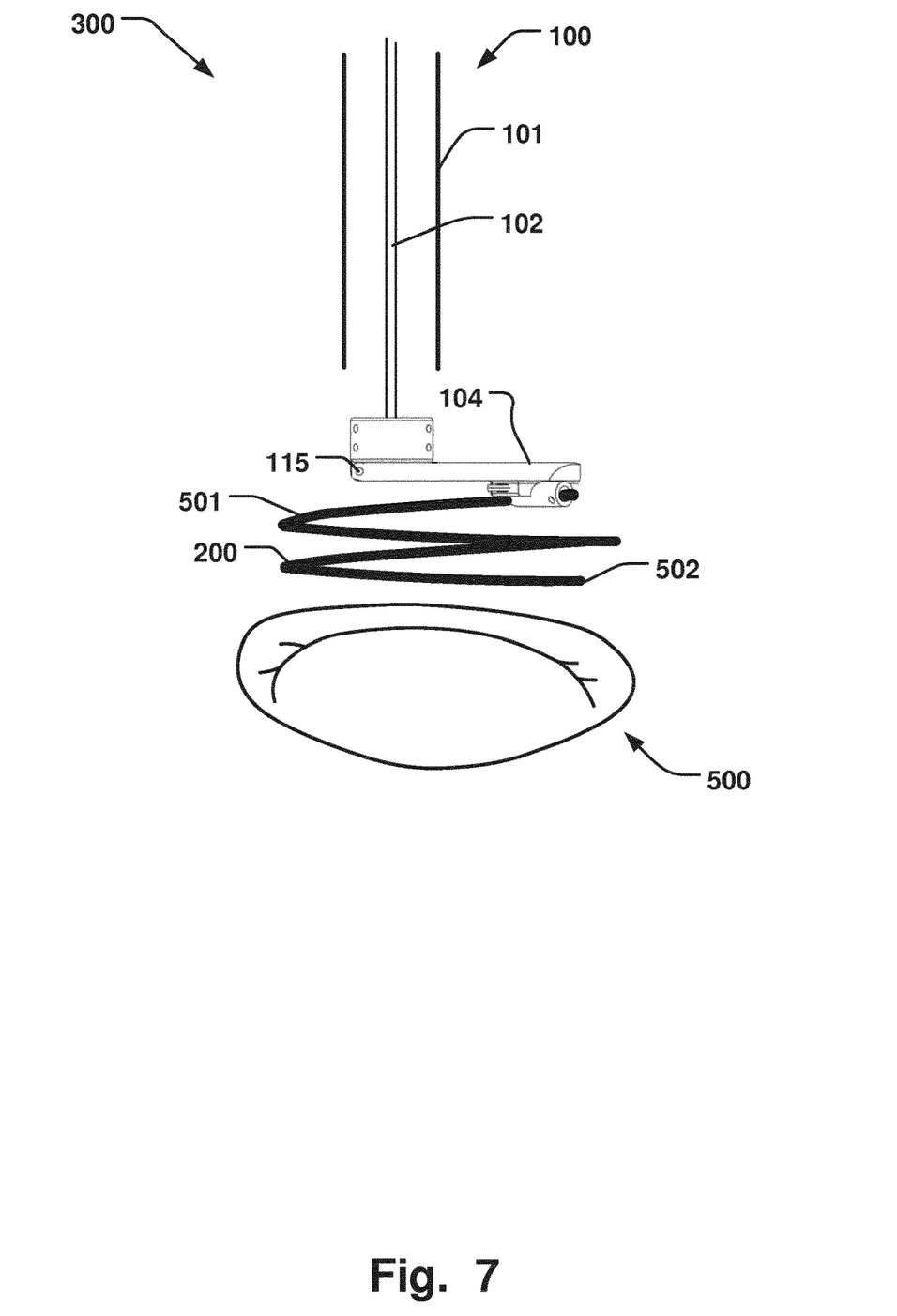
FIG. 7 is a schematic illustration, in a perspective view, of a delivery device holding an annuloplasty implant at a heart valve according to one example.
Figure 9:
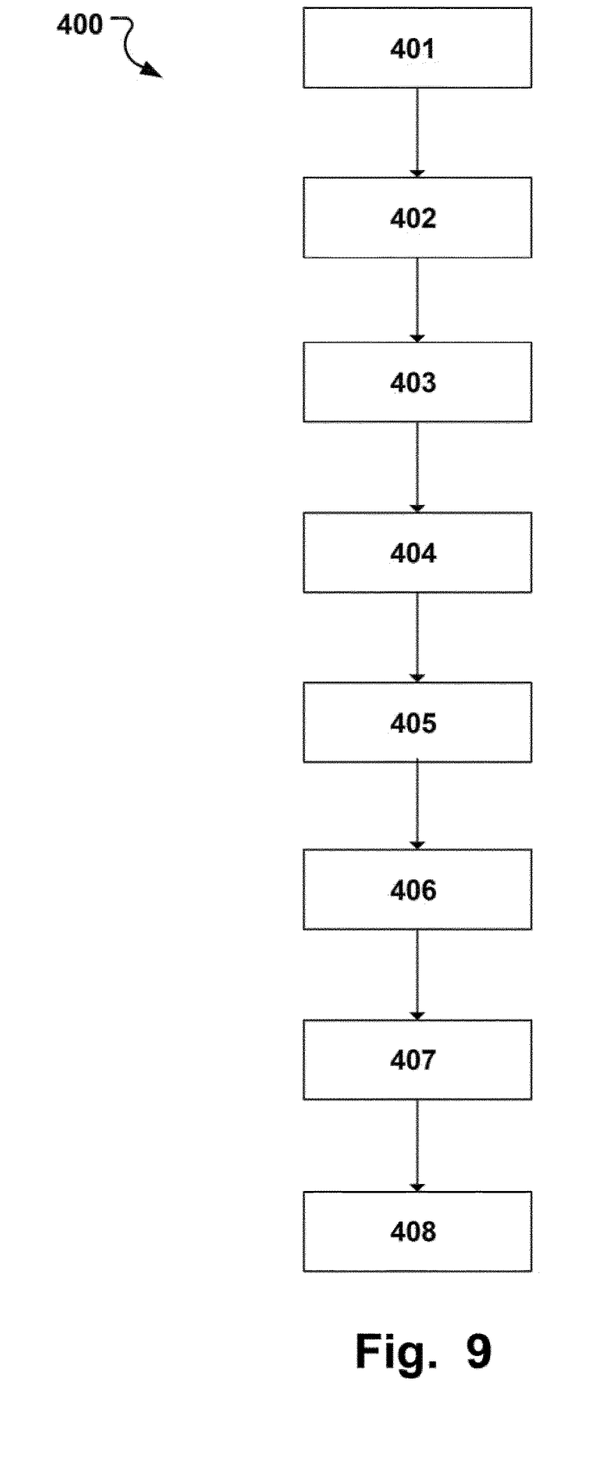
FIG. 9 is a flow-chart of a method of delivering an annuloplasty implant at a target site in the heart according to one example.

A method 400 is provided for delivering an annuloplasty implant 200 with a delivery device 100. The method 400 is schematically illustrated in FIG. 9. The order in which the steps are described should not be construed as limiting, and it is conceivable that the order of the steps may be varied depending on the particular procedure. The delivery device 100 has a holder 104 as described in the examples above, being pivotably connected to the distal portion 105 of the delivery wire 102 inside the sheath 101. The holder 104 is releasably connectable to the implant 200. The method 400 comprises holding 401 the implant 200 inside the sheath 101 whereby the holder 104 is folded inside the sheath 101 in a delivery configuration; moving 402 the holder 104 distally out of the sheath 101 whereby the implant 200, being formed from a shape memory material assumes a pre-defined shape; and folding 403 the holder 104 from a the delivery configuration to an expanded deployed configuration outside the sheath 101 whereby the implant 200 is pivoted 404 by the holder 104 into position at a heart valve 500. FIG. 7 illustrates an example where the implant 200 has been pivoted into the correct position adjacent the heart valve 500. In this example, the implant 200 is a helix-shaped implant. The implant 200 may then be rotated into the correct position through the valve 500, so that the ring-shaped supports of the helix implant are positioned on either side of the heart valve leaflets.

Thus, the annuloplasty implant 200 may be a helix ring and the method may comprise holding 405 the helix ring 200 at a periphery 118 thereof at a distance 119 from a central axis 103' of the sheath 101 in the expanded deployed configuration; turning 406 the helix ring 200 into the valve 500 by a rotating motion such that a first 501 and second 502 support members are positioned on each side of the heart valve leaflets; disconnecting 407 the implant 200 from the holder 104; and folding 408 the holder 104 inside the outer sheath 101 in the delivery configuration. The delivery device 100 can then subsequently be withdrawn from the target site. This provides for the above mentioned advantages ultimately allowing for increased maneuverability, facilitating the positioning of the helix implant 200 at the valve and further reducing the time the procedure and increasing patient safety. FIG. 8*b* illustrates another example of positioning the delivery device 100, as described with reference to FIGS. 6*a-b* and 8*a,* at the heart valve 500.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A delivery device for an annuloplasty implant comprising:
   an outer sheath,
   a delivery wire being movable within said outer sheath in a longitudinal direction thereof, and
   a holder being releasably connectable to said implant, said holder being pivotably connected to a distal portion of said delivery wire,
   wherein said holder is folded inside said outer sheath in a delivery configuration,
   wherein said holder is foldable from said delivery configuration to an expanded deployed configuration outside said outer sheath,
   wherein the holder is configured to push the implant outside the sheath, when connected to the holder, so that the implant is movable to a relaxed shape outside the sheath,
   wherein the holder is connectable to the implant so that the implant, when in the relaxed shape, is rotatable with the holder relative the delivery wire when moving the holder from the delivery configuration to the expanded deployed configuration and
   a width of said holder corresponds substantially to the diameter of said outer sheath.

2. The delivery device according to claim 1, wherein said holder is elongated and is extending in said longitudinal direction in said delivery configuration, and extending in a radial direction, perpendicular to said longitudinal direction, in said expanded deployed state.

3. The delivery device according to claim 1, comprising a control member, connected to said holder, whereby actuation of said control member moves said holder from said delivery configuration to said expanded deployed configuration by a pivoting motion.

4. The delivery device according to claim 1, wherein said holder comprises a connecting unit that is adapted to releasably connect to said implant, wherein said connecting unit is arranged at a distal end of said holder.

5. The delivery device according to claim 4, wherein said delivery wire is rotatable relative said outer sheath, wherein said connecting unit is adapted to apply a force at a peripheral portion of said implant, at a distance from a central axis of said outer sheath when said implant, in use, is held by said holder in said expanded deployed configuration, such that said force can bring said implant into rotation about said central axis.

6. The delivery device according to claim 2, wherein a length of said elongated holder corresponds substantially to a radius (r) of said implant, when said implant, in use, is held by said holder in said expanded deployed configuration and said implant has a general ring shape with said radius (r).

7. The delivery device according to claim 6, wherein said connecting unit is adapted to connect to an end portion of said implant, and said connecting unit is aligned at a distal end of said holder so that a proximal end of said holder is positioned substantially at the center of said implant, when said implant, in use, is held by said holder in said expanded deployed configuration and said implant has a general ring shape with said center.

8. The delivery device according to claim 1, wherein said connecting unit is connected to a release unit, whereby actuation of said release unit releases said implant from said holder by disengaging an implant lock.

9. The delivery device according to claim 8, wherein said implant lock is engageable with an end portion of said implant, when said implant, in use, is held by said holder.

10. The delivery device according to claim 1, wherein said holder is pivotably connected at a pivot joint arranged at said distal portion of said delivery wire, wherein said pivot joint is arranged at a periphery of said distal portion in a radial direction, perpendicular to said longitudinal direction.

11. The delivery device according to claim 2, wherein said holder has a first and a second pivotable portion, each being expandable in radially opposite directions in said expanded deployed configuration along said radial direction.

12. The delivery device according to claim 3, wherein said control member is a control wire.

13. The delivery device according to claim 8, wherein said release unit is a release wire.

14. A delivery device for an annuloplasty implant comprising:
   an outer sheath;
   a delivery wire being movable within said outer sheath in a longitudinal direction thereof;
   a holder being releasably connectable to said implant, said holder being pivotably connected to a distal portion of said delivery wire; and
   a control member, connected to said holder, whereby actuation of said control member moves said holder from said delivery configuration to said expanded deployed configuration by a pivoting motion,
   wherein said holder is folded inside said outer sheath in a delivery configuration,
   wherein said holder is foldable from said delivery configuration to an expanded deployed configuration outside said outer sheath, wherein the holder is configured to push the implant outside the sheath, when connected to the holder, so that the implant is movable to a relaxed shape outside the sheath, wherein the holder is connectable to the implant so that the implant, when in the relaxed shape, is rotatable with the holder relative the delivery wire when moving the holder from the delivery configuration to the expanded deployed configuration, and wherein said holder has a first and a second pivotable portion, each being expandable in radially opposite directions in said expanded deployed configuration along said radial direction, each of said first and second pivotable portions comprising foldable proximal and distal sections forming V-shaped first and second pivotable portions having an apex at a radially outward position and a base at a radially inward position, and wherein a length of said base is adjustable by moving said control member relative said delivery wire, whereby said proximal and distal sections are foldable between said delivery configuration and said expanded deployed configuration by adjusting the length of said base.

15. The delivery device according to claim 14, wherein said holder is elongated and is extending in said longitudinal direction in said delivery configuration, and extending in a radial direction, perpendicular to said longitudinal direction, in said expanded deployed state.

16. The delivery device according to claim 14, wherein said holder comprises a connecting unit that is adapted to releasably connect to said implant, wherein said connecting unit is arranged at a distal end of said holder.

17. The delivery device according to claim 16, wherein said delivery wire is rotatable relative said outer sheath, wherein said connecting unit is adapted to apply a force at a peripheral portion of said implant, at a distance from a central axis of said outer sheath when said implant, in use, is held by said holder in said expanded deployed configuration, such that said force can bring said implant into rotation about said central axis.

18. The delivery device according to claim 15, wherein a length of said elongated holder corresponds substantially to a radius (r) of said implant, when said implant, in use, is held by said holder in said expanded deployed configuration and said implant has a general ring shape with said radius (r).

19. The delivery device according to claim 18, wherein said connecting unit is adapted to connect to an end portion of said implant, and said connecting unit is aligned at a distal end of said holder so that a proximal end of said holder is positioned substantially at the center of said implant, when said implant, in use, is held by said holder in said expanded deployed configuration and said implant has a general ring shape with said center.

20. The delivery device according to claim 14, wherein said connecting unit is connected to a release unit, whereby actuation of said release unit releases said implant from said holder by disengaging an implant lock.

21. The delivery device according to claim 20, wherein said implant lock is engageable with an end portion of said implant, when said implant, in use, is held by said holder.

22. The delivery device according to claim 14, wherein a width of said holder corresponds substantially to the diameter of said outer sheath.

23. The delivery device according to claim 14, wherein said holder is pivotably connected at a pivot joint arranged at said distal portion of said delivery wire, wherein said pivot joint is arranged at a periphery of said distal portion in a radial direction, perpendicular to said longitudinal direction.

24. The delivery device according to claim 15, wherein said holder has a first and a second pivotable portion, each being expandable in radially opposite directions in said expanded deployed configuration along said radial direction.

25. The delivery device according to claim 14, wherein said control member is a control wire.

26. The delivery device according to claim 20, wherein said release unit is a release wire.

* * * * *